(12) United States Patent
Rege et al.

(10) Patent No.: US 10,045,703 B2
(45) Date of Patent: Aug. 14, 2018

(54) ANISOTROPIC PROCESSING OF LASER SPECKLE IMAGES

(71) Applicant: THE JOHNS HOPKINS UNIVERSITY, Baltimore, MD (US)

(72) Inventors: Abhiskek Rege, Baltimore, MD (US); Janaka Senarathna, Baltimore, MD (US); Nitish V. Thakor, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 595 days.

(21) Appl. No.: 14/346,984

(22) PCT Filed: Sep. 26, 2012

(86) PCT No.: PCT/US2012/057221
§ 371 (c)(1),
(2) Date: Mar. 25, 2014

(87) PCT Pub. No.: WO2013/049123
PCT Pub. Date: Apr. 4, 2013

(65) Prior Publication Data
US 2014/0316284 A1    Oct. 23, 2014

Related U.S. Application Data

(60) Provisional application No. 61/539,042, filed on Sep. 26, 2011.

(51) Int. Cl.
*A61B 5/026* (2006.01)
*A61B 5/00* (2006.01)

(52) U.S. Cl.
CPC .......... *A61B 5/0261* (2013.01); *A61B 5/0059* (2013.01); *A61B 5/0062* (2013.01);
(Continued)

(58) Field of Classification Search
None
See application file for complete search history.

(56) References Cited

U.S. PATENT DOCUMENTS 7,113,817 B1 * 9/2006 Winchester, Jr. .... A61B 3/1233
356/27
2007/0248265 A1 * 10/2007 Lundstrom .......... G06K 9/0053
382/168
(Continued)

FOREIGN PATENT DOCUMENTS

CN       101784227 A     7/2010
WO     2010096447 A2     8/2010

*Primary Examiner* — Katherine Fernandez
*Assistant Examiner* — Bradley Impink
(74) *Attorney, Agent, or Firm* — Saul Ewing Arnstein & Lehr LLP; Gianna Julian-Arnold

(57) ABSTRACT

An embodiment in accordance with the present invention provides a system and method for imaging living tissue and processing laser speckle data anisotropically to calculate laser speckle contrast preferentially along the direction of blood flow. In the present invention, raw laser speckle images are obtained and processed resulting in the anisotropic laser speckle images. The system and method involve the determination of the direction of blood flow for every pixel within the region of interest (primary pixel) and subsequent extraction of a set of secondary pixels in the spatio-temporal neighborhood of the primary pixel that is anisotropic in the direction of blood flow. Speckle contrast is then calculated for every primary pixel as the ratio of standard deviation and mean of all secondary pixels in this anisotropic neighborhood and collectively plotted using a suitable color mapping scheme to obtain an anisotropic laser speckle contrast image of the region of interest.

19 Claims, 7 Drawing Sheets

(52) U.S. Cl.
CPC .......... *A61B 5/0066* (2013.01); *A61B 5/0042* (2013.01); *A61B 5/489* (2013.01)

(56) References Cited

U.S. PATENT DOCUMENTS

2010/0280315 A1 11/2010 Pan
2011/0013002 A1 1/2011 Thompson et al.

\* cited by examiner

ANISOTROPIC PROCESSING OF LASER SPECKLE IMAGES

CROSS REFERENCE TO RELATED APPLICATIONS

This application claims the priority of PCT/US2012/057221, filed on Sep. 26, 2012, which claims the benefit of priority to United States Application No. 61/539,042, filed on Sep. 26, 2011, the entire contents of each of which are hereby incorporated in total by reference.

CROSS REFERENCE TO RELATED APPLICATIONS

This application claims the benefit of U.S. Provisional Patent Application No. 61/539,042, filed Sep. 26, 2011, which is incorporated by reference herein, in its entirety.

GOVERNMENT SUPPORT

This invention was made with government support under grants UL1RR025005 and R21EB012829-01A1 awarded by the National Institutes of Health. The government has certain rights in the invention.

FIELD OF THE INVENTION

The present invention relates generally to medical imaging. More particularly, the present invention relates to a method of laser speckle imaging.

BACKGROUND OF THE INVENTION

Laser speckle contrast imaging (LSCI) is a non-scanning, wide-field technique useful in visualizing blood vessels and blood flow without the introduction of any exogenous contrast agents. It has been widely used in neuroscience research. Incidence of coherent illumination on living tissue gives rise to interference patterns called speckles. When this speckle pattern is photographed, the movement of red blood cells within blood vessels causes a blurring effect over the exposure time of the imaging camera. Such a blur can be quantified in terms of a quantity called laser speckle contrast (K) at each pixel $P_0(x_0,y_0,n_0)$ using:

$$K(P_0) = \frac{\sigma_{N(P_0)}}{\mu_{N(P_0)}}$$

Where $\sigma_{N(P_0)}$ and $\mu_{N(P_0)}$ are the standard deviation and mean respectively of the intensities of all pixels in a defined local neighborhood $N(P_0)$ of $P_0$; and $(x_0,y_0,n_0)$ denote the location of the pixel in the spatial (x-y) plane of the image and the number of the sequentially acquired image frame n. Traditionally, N is chosen in either exclusively the spatial domain (called sLSCI herein) or exclusively the temporal domain (called tLSCI herein). tLSCI optimizes spatial resolution by compromising temporal resolution, while sLSCI optimizes temporal resolution by compromising the spatial resolution.

Because traditional speckle contrast processing schemes use pixel neighborhoods that are isotropic in the spatial domain, often a square of pixels, accurate representation of blood velocity is confounded. This is because blood velocity changes steeply along the diameter of the vessel. However, blood flow within blood vessels with diameters less than approximately 200 micrometers is orderly and aligned along the axial direction of these vessels. The axial direction for a vessel is clarified as the direction parallel to the centerline and perpendicular to the diameter of the vessel in consideration. Further, the change in blood velocities along the axial direction is minimal. Thus, speckle blurring is expected to show directional sensitivity, allowing for preferential processing of speckle data along the direction of blood flow thereby preventing the loss of spatial resolution or any radial confounding of the signal. Further, this allows for reducing the size of the neighborhood in the temporal domain, while still retaining enough pixels in the neighborhood to obtain reliable estimation of the local K values, thereby significantly improving the temporal resolution. Techniques have previously been reported that utilize isotropic approaches to address the issue of spatiotemporal resolution. Temporally averaged spatial speckle contrast calculation, (called $t_{avg}$sLSCI herein) and spatially averaged temporal speckle contrast calculation, (called $s_{avg}$tLSCI herein) achieve robustness by smoothing sLSCI and tLSCI images in the temporal and spatial domains respectively. Three dimensional spatiotemporal processing, (called stLSCI herein) uses a cuboid of pixels in the spatiotemporal domain as the neighborhood in which local K values are calculated.

It would therefore be advantageous to provide a system and method that can achieve both high spatial resolution as well as high temporal resolution, so that rapid flow changes could be monitored at the level of microvessels or conversely the image acquisition time be commensurately reduced. It would also be advantageous to provide a system and method to calculate local speckle contrast along an estimated direction of blood flow at each pixel, while using a few frames along the temporal dimension, thus keeping the window two-dimensional in the spatiotemporal domain.

SUMMARY OF THE INVENTION

The foregoing needs are met, to a great extent, by the present invention, wherein in one aspect, a system for obtaining a laser speckle contrast image includes a device configured for the acquisition of a predetermined number of raw laser speckle images and a processor configured to receive the raw laser speckle images. The processor is configured to select a primary pixel in the raw laser speckle image and estimate a direction of blood flow at said primary pixel. Additionally, the processor is configured to obtain an anisotropic local neighborhood that is aligned along the direction of blood flow and calculate a local speckle contrast value at the primary pixel within the anisotropic local neighborhood. Also, the processor is configured to generate an anisotropic laser speckle contrast image of the region of interest using the local speckle contrast values of all pixels in the region of interest.

In accordance with an aspect of the present invention, the device configured for the acquisition of a predetermined number of raw laser speckle images includes a source of coherent illumination, an optical assembly, and an image acquisition system. The source of coherent illumination can take the form of one or more of a gas, a diode, and a pulsed laser. The image acquisition system can take the form of any of various types of charge coupled device (CCD) cameras, various types of metal oxide semiconductor (MOS) or complementary MOS (CMOS) cameras, various types of photodiodes, phototransistors and photo tubes. Additionally, the device for acquisition of the predetermined number of raw laser speckle images can use light with a wavelength of illumination in a range of approximately 100 nm to approximately 2000 nm. The predetermined number of raw laser speckle images is in a range of between 1 and as many images as can be acquired in approximately 60 seconds of image acquisition time, and the processor is further configured to select an anisotropic local neighborhood comprising a set of secondary pixels aligned along the direction of blood flow. The processor could take the form of one or more of a computer, microprocessor, microcontroller, field programmable gate array (FPGA), complex programmable logic device (CPLD) and application specific integrated circuit (ASIC).

In accordance with another aspect of the present invention, the number of secondary pixels in the set of secondary pixels may be predetermined or dynamically determined during the course of imaging to be at least two in every image frame and limited by the total number of pixels acquired in every image frame. The processor is further configured to calculate the local speckle contrast value as the ratio of standard deviation of all secondary pixel intensities and the mean of all secondary pixel intensities within the said anisotropic local neighborhood. The anisotropic local neighborhood can also be planar in the spatio-temporal domain and mathematically expressible in the form:

$$N(P_0) = \begin{Bmatrix} P(x, y, n) \\ \text{such} \ldots \text{that} \\ |(n - n_0)| \leq \delta_N, \\ \|(x, y) - (x_0, y_0)\| \leq \delta_L, \\ \arg[(x, y) - (x_0, y_0)] = \arg[\ell_0] \end{Bmatrix}$$

Where n denotes the frame number in the acquired image stack, (x, y) denote pixel coordinates in the image plane, $P_0(x_0, y_0, n_0)$ is the chosen pixel of interest (primary pixel), $\ell_0$ represents the direction of the blood flow at $P_0$, while $\delta_N$ and $\delta_L$ are predetermined parameters that govern the number of frames and number of pixels in each frame respectively that are used for processing, and $N(P_0)$ is the said anisotropic local neighborhood that includes the set of secondary pixels P(x, y, n) including $P_0$ itself.

In accordance with still another aspect of the present invention, the anisotropic local neighborhood can take the form of one or multiple adjacent surfaces of pixels in the spatio-temporal domain that are aligned along the direction of blood flow and in a manner that the projection of the surface or surfaces in the plane of the image may be a smooth curve. Further, the anisotropic local neighborhood may also be one or more composite collections of piece-wise planar neighborhoods of pixels in the spatio-temporal domain that are aligned along the direction of blood flow and in a manner that the projection of the surface or surfaces in the plane of the image may be piece-wise linear. Applications and uses of the system can include, but are not limited to imaging of blood flow in tissue, imaging of vascular morphology in tissue, imaging of changes in vascular morphology in tissue, imaging of changes in blood flow in tissue, imaging of the tissue in natural form, in a disease state, or in a form that is altered for therapy or experimentation or for the sake of monitoring, imaging of tissue that is stabilized using anesthesia or paralytics or non-stablized, imaging of tissue perfusion in a manner that blood vessels are not discernible to the human eye but blood flow is discernible. Further, the system may comprise one or more output devices for display or printing, one or more data storage devices for temporarily or permanently storing, and one or more transmission devices for transmitting over wired and wireless communication channels, the raw laser speckle images, intermediate data or generated the anisotropic laser speckle contrast images. The system may comprise an interface device that may allow users to control imaging parameters.

In accordance with another aspect of the present invention, a method for obtaining a laser speckle contrast image includes acquiring a predetermined number of raw laser speckle images and selecting a primary pixel in one of the predetermined number of raw laser speckle images. The method also includes determining a direction of blood flow at the primary pixel and obtaining an anisotropic local neighborhood that is aligned preferentially along the direction of blood flow. Additionally, the method includes calculating a local speckle contrast value at the primary pixel within the anisotropic local neighborhood. Further, the method includes generating an anisotropic laser speckle contrast image using the local speckle contrast value.

In accordance with yet another aspect of the present invention, the predetermined number of raw laser speckle images may be acquired under sequential or simultaneous illumination comprising one or more wavelengths lying in the approximate range of 200 nm to 2000 nm. The number of raw laser speckle images utilized for anisotropic laser speckle contrast calculation is in a range of between approximately 1 and as many images as can be acquired in 60 seconds of image acquisition time. Additionally, the method includes estimating the direction of blood flow using information about the axial direction of blood vessels calculated for each pixel that lies inside a vessel. The method can also include selecting a set of secondary pixels along the direction of blood flow wherein the number of secondary pixels may be predetermined or dynamically determined during the course of imaging to be at least two in every image frame and limited by the total number of pixels acquired in every image frame.

In accordance with still another aspect of the present invention, the method includes calculating the local speckle contrast value as the ratio of standard deviation of all pixel intensities and the mean of all pixel intensities within the said anisotropic local neighborhood. The method can further include extracting the anisotropic local neighborhood which is planar in the spatio-temporal domain and mathematically expressible in the form:

$$N(P_0) = \begin{Bmatrix} P(x, y, n) \\ \text{such} \ldots \text{that} \\ |(n - n_0)| \leq \delta_N, \\ \|(x, y) - (x_0, y_0)\| \leq \delta_L, \\ \arg[(x, y) - (x_0, y_0)] = \arg[\ell_0] \end{Bmatrix}$$

where n denotes the frame number in the acquired image stack, (x, y) denote pixel coordinates in the image plane, $P_0(x_0, y_0, n_0)$ is the pixel of interest chosen, $l_0$ represents the direction of the blood flow at $P_0$, while $\delta_N$ and $\delta_L$ are predetermined parameters that govern the number of frames and number of pixels in each frame respectively that are used for processing, and $N(P_0)$ is the said anisotropic local neighborhood.

In accordance with another aspect of the present invention, the method includes extracting an anisotropic local neighborhood that may be one or multiple adjacent surfaces of pixels in the spatio-temporal domain that are aligned along the direction of blood flow and in a manner that the projection of the surface or surfaces in the plane of the image may be a smooth curve. The method can alternately be executed by extracting an anisotropic local neighborhood that may be one or more composite collections of piece-wise planar neighborhoods of pixels in the spatiotemporal domain that are aligned along the direction of blood flow and in a manner that the projection of the surface or surfaces in the plane of the image may be piece-wise linear. The method can include extracting the direction using one selected from the group consisting of manual estimation, ridge based detection, curvature analysis and region growing approach. In addition, the method can include extracting the direction with minimum spatial contrast or spatial gradient of pixel intensities incurred in the neighborhood of the said primary pixel while traversing all possible or a predetermined set of likely directions of blood flow.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

Figure 1:
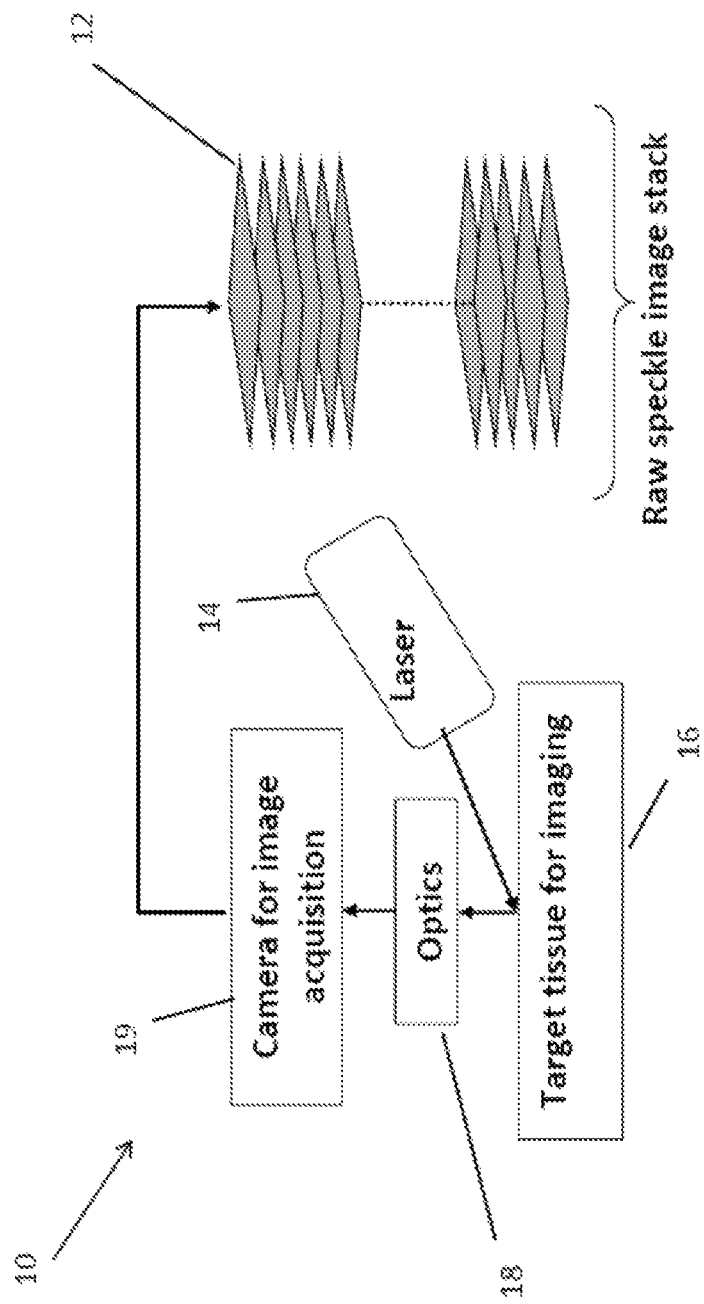
FIG. 1 illustrates a schematic diagram of an anisotropic laser speckle contrast imaging (aLSCI) apparatus and resultant image stack according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment, in accordance with the present invention, provides a system and method for obtaining anisotropic laser speckle contrast images. In the present invention, raw laser speckle images are obtained and processed resulting in the anisotropic laser speckle contrast image. In order to process the raw laser speckle images, a primary pixel in the raw laser speckle image is selected for subsequent steps. The direction of blood flow at said primary pixel is determined and used to obtain a local anisotropic neighborhood of pixels in the spatio-temporal domain, that aligns with the estimated direction of blood flow at the primary pixel. Subsequently, the anisotropic laser speckle contrast is calculated at the primary pixel by utilizing the pixels in this chosen anisotropic neighborhood. This process of direction estimation, neighborhood extraction and contrast calculation can be repeated for all pixels in either the entire field of view of the image or in a selected region (area) of interest within the image. An anisotropically processed laser speckle contrast image (aLSCI image) is then made using the local speckle contrast values for the pixels.

Because blood flow within microvessels is orderly and aligned along a central axis of the blood vessel, speckle blurring displays directional sensitivity. Traditional speckle contrast calculation schemes employ spatially-isotropic neighborhoods that are usually square in the spatial domain or cuboidal in the spatio-temporal domain. Thus, accurate representation of blood velocity is confounded in traditionally used contrast calculation schemes, as velocity changes steeply along the diameter of the vessel. However, the change in blood velocities along the length (axial direction) of vessels is minimal, allowing for preferential processing of speckle data along the direction of blood flow thereby preventing the loss of spatial resolution or any radial confounding of the blood flow estimates. Further, such anisotropic processing of speckle data allows for reduction of the neighborhood size in the temporal domain, while still retaining enough pixels to obtain reliable estimation of a local laser speckle contrast value (K), improving the temporal resolution. In the anisotropic laser speckle contrast imaging protocol described herein, the local speckle contrast value (K) is calculated along an estimated direction of blood flow at each pixel of interest, while using a stack of raw laser speckle image frames along the temporal dimension. Thus, the pixel neighborhood is two-dimensional in the spatiotemporal domain.

FIG. 1 illustrates a schematic diagram of an anisotropic laser speckle contrast imaging (aLSCI) apparatus and resultant image stack according to an embodiment of the present invention. As shown in FIG. 1, the equipment 10 used to capture the raw laser speckle images 12 includes a coherent light source 14 illuminating the desired region of interest (ROI) on the target tissue 16. The coherent light source 14 can take the form of, for example, a 632 nm red laser, or any other suitable laser known to or conceivable by one of skill in the art, including a gas, diode, or pulsed laser. Additionally, any wavelength of illumination known to or conceivable by one of skill in the art can be used, such as, for example, illumination in the visible and near-visible spectrum, from approximately 200 nm to approximately 2000 nm. The target tissue 16 can take the form of any living or diseased tissue that would need to be imaged, known to or conceivable by one of skill in the art. The target tissue may include but is not limited to the retina, skin, brain, heart, lungs, or muscle. The target tissue can further be in its natural form, in a disease state, altered for experimentation or therapy; or prepared for imaging. The target tissue need not be human, and imaging can be done for any living organism chosen by or of interest to one of skill in the art. An optical assembly 18 is used to magnify or de-magnify the tissue, as deemed necessary by the operator or processor controlling the imaging session. The processor can be automated, semi-automated, manual, or have any combination of these characteristics, as is known to or conceivable to one of skill in the art. The optical assembly may be used to control other imaging parameters such as numerical aperture, size of speckle (that is, the diameter of the Airy disc) and the desired depth of field or depth of focus. Such an optical assembly may include lenses, apertures, mirrors, beam splitters, dichroic mirrors, and polarizers. The optical assembly 18 can take the form of any suitable assembly known to or conceivable by one of skill in the art, and can be tailored to the type of tissue being imaged. For example, an optical assembly that mimics a fundus camera can be used for retinal imaging, while an optical assembly that can be used to image the brain will be described in further detail with respect to the example detailed below.

The sequentially acquired stack of raw laser speckle images 12, illustrated in FIG. 1 can be acquired using a camera 19 known to or conceivable by one of skill in the art, such as a CCD or CMOS camera, or a photomultiplier tube. As illustrated in FIG. 1, a time-stack of raw laser speckle images 12 can be acquired under laser illumination using the equipment setup 10. The time over which the image acquisition device integrates photons for every exposure (that is, the exposure time of the camera) may be set to a predetermined value or set dynamically during the course of imaging. A frame can be acquired with an exposure time ranging from 1 microsecond to 10 seconds. Any number of raw laser speckle images 12 can be taken, as determined by one of skill in the art. The number of laser speckle images 12 taken will be discussed further, herein. One of skill in the art can alter the size and embodiment of the equipment 10, as needed for different tissue imaging tasks. For example, the equipment 10 can take the form of any one of a bench top setup, a portable handheld device for diagnostics or research, on-body imaging devices, such as a head-mounted imager for neuroscience research, or any other suitable configuration, known to or conceivable by one of skill in the art.

Figure 2:
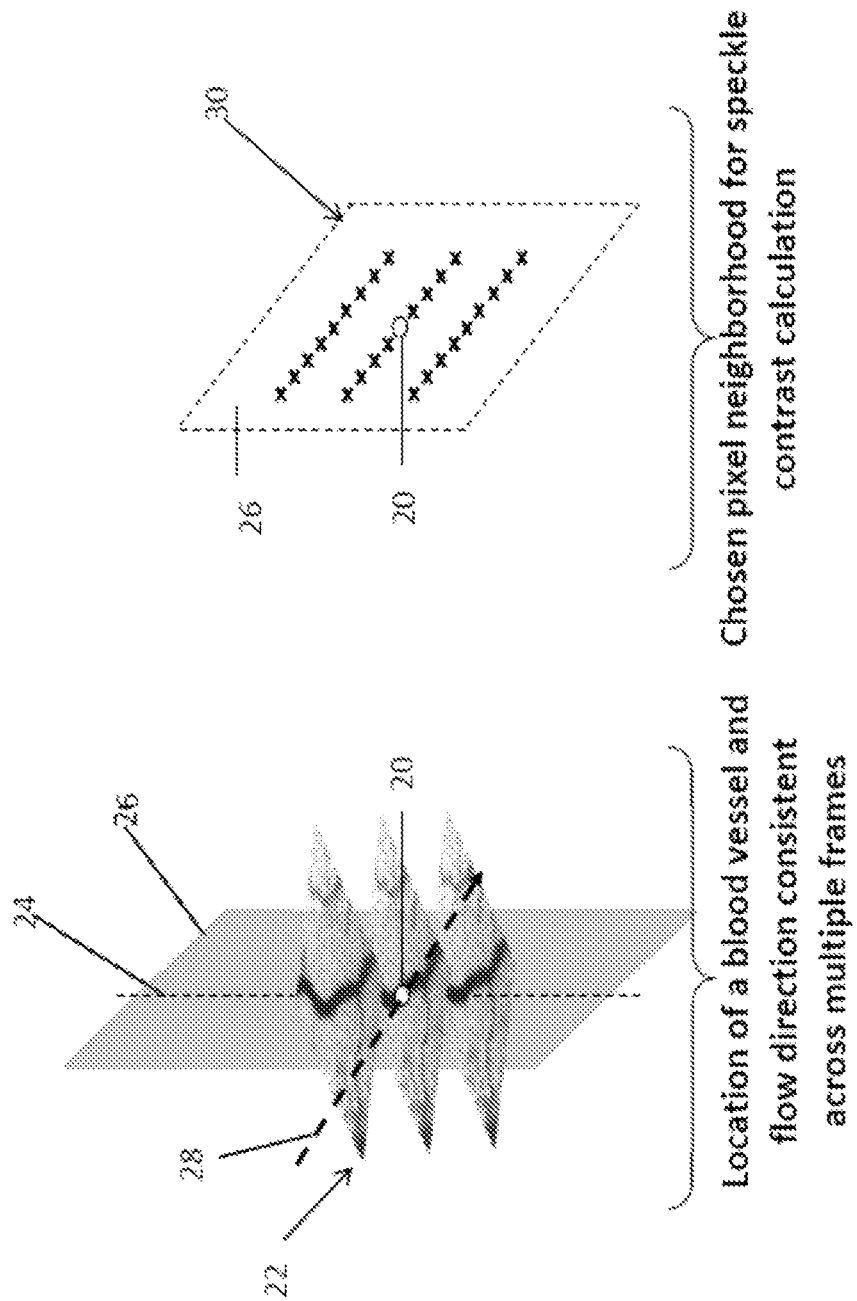
FIG. 2 illustrates a schematic diagram of the principle of anisotropic laser speckle contrast imaging using an anisotropic neighborhood of pixels aligned along the direction of flow according to an embodiment of the present invention.

FIG. 2 illustrates a schematic diagram of a location and orientation of an exemplary individual blood vessel across three raw laser speckle images, according to an embodiment of the present invention. A pixel of interest $P_0(x_0, y_0, n_0)$ 20, disposed in the individual blood vessel, is highlighted across three of the raw laser speckle images 22. While $(x_0, y_0)$ indicates the spatial location of the pixel in the image plane, $n_0$ indicates the image frame number (in the time domain) in which the pixel is located. A plane 24 that is both perpendicular to the image plane as well as along the direction of blood flow shown by axis 28 at $P_0$ 20, shows the spatiotemporal (2D) plane along a direction of flow. The direction of blood flow along axis 28 may also be estimated using the axis of the blood vessel, which is parallel to the centerline or edges of the vessel and perpendicular to the diameter of the vessel. The location of the blood vessel and the axis of the direction of blood flow 28 are generally consistent across the three raw laser speckle images 22. In event that the acquired stack of raw laser speckle images are not perfectly registered, an intermediate step of inter-frame registration may be used.

FIG. 2 also illustrates a pixel neighborhood spanning the three raw laser speckle images that is chosen for performing a calculation of a laser speckle contrast. As illustrated in FIG. 2, a neighborhood of pixels 30 is chosen around $P_0$ 20, in a spatio-temporal plane 26. The chosen neighborhood 30 spans the three raw laser speckle images 22, with nine pixels in each image frame, along the direction of the axis of blood flow 28. In each frame, four pixels in the chosen neighborhood 30 are on either side of $P_0$ 20. The neighborhood of pixels 30 is anisotropic since it has a preferential orientation along the direction of blood flow. This preserves spatial resolution along the diameter of the vessel, while capturing the blurring of speckles in an effective manner.

Figure 3:
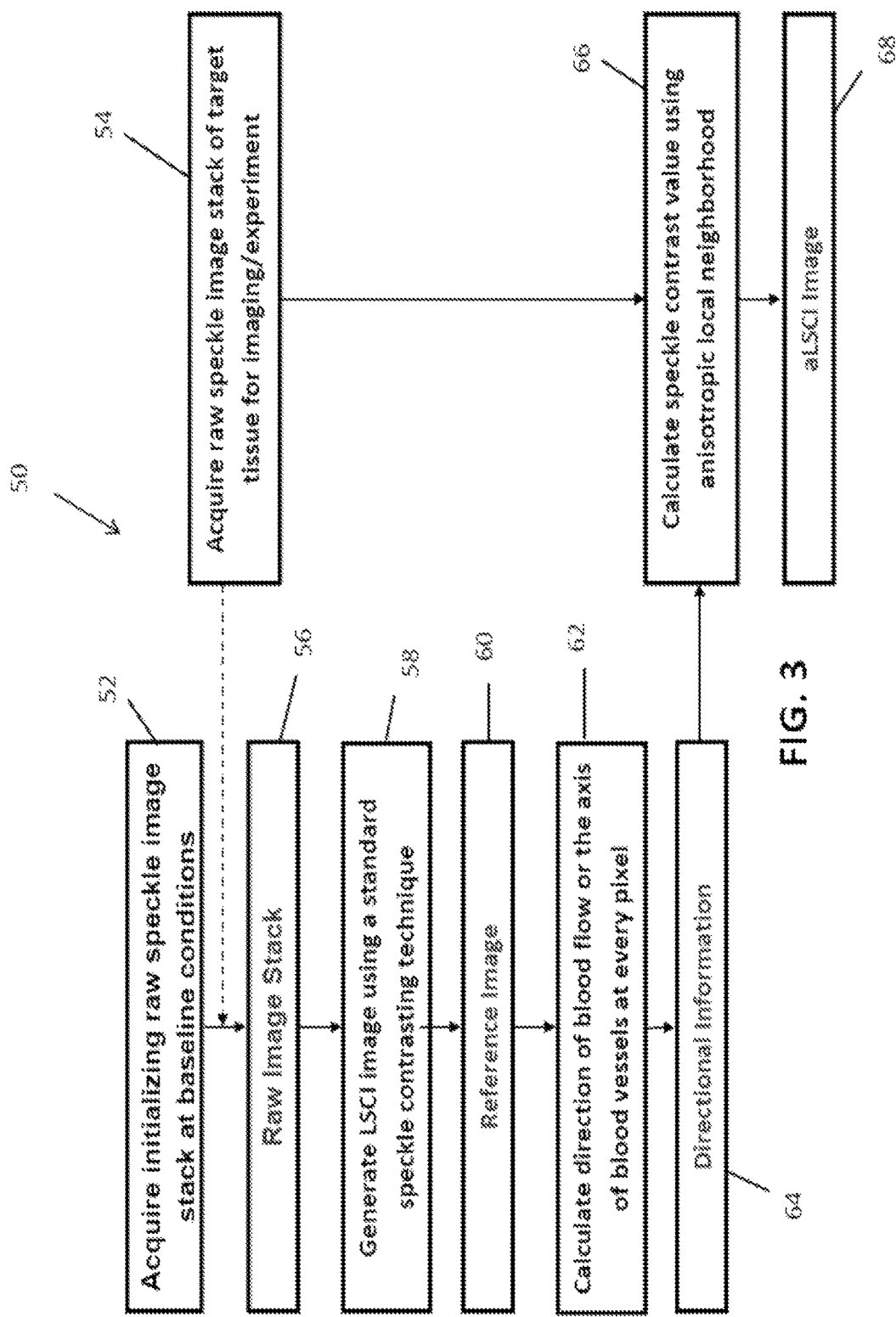
FIG. 3 illustrates a flow diagram of a method of acquiring an anisotropic laser speckle contrast image, according to an embodiment of the present invention.

FIG. 3 illustrates a flow diagram of a method of acquiring an anisotropic laser speckle contrast (aLSCI) image, according to an embodiment of the present invention. The method 50 includes a step 52 of acquiring an initializing stack of raw speckle images of the target tissue at baseline conditions and a step 54 of acquiring a raw speckle image stack of target tissue dynamically during the experimentation/imaging session. In other words, the stack of raw speckle images required for subsequent processing can be obtained separately, exclusively for initialization, through step 52, or the same stack of images obtained in step 54 can also be used for this purpose. Step 56 includes forming a raw image stack from the raw images obtained in steps 52 and/or 54. The raw laser speckle image stack is used to generate a laser speckle contrast image (LSCI) using a traditional speckle contrast calculation scheme (sLSCI, tLSCI, stLSCI, $s_{avg}$tLSCI or $t_{avg}$sLSCI or any combination thereof) in step 58, resulting in the reference image of step 60. Step 62 includes calculating a direction of blood flow with or without determining an axial direction of the blood vessel for every pixel, resulting in the directional information of step 64. This directional information can then be used to identify and select an anisotropic local neighborhood and calculate the anisotropic laser speckle contrast, as in step 66. Step 68 includes using the laser speckle contrast values of all pixels to create an aLSCI image. The resultant image can be produced in grayscale or using a custom color mapping scheme. It should be noted that the method illustrated in FIG. 3 can be performed either sequentially for every pixel or simultaneously for multiple pixels using matrix calculations, or any combination thereof.

Figure 4:
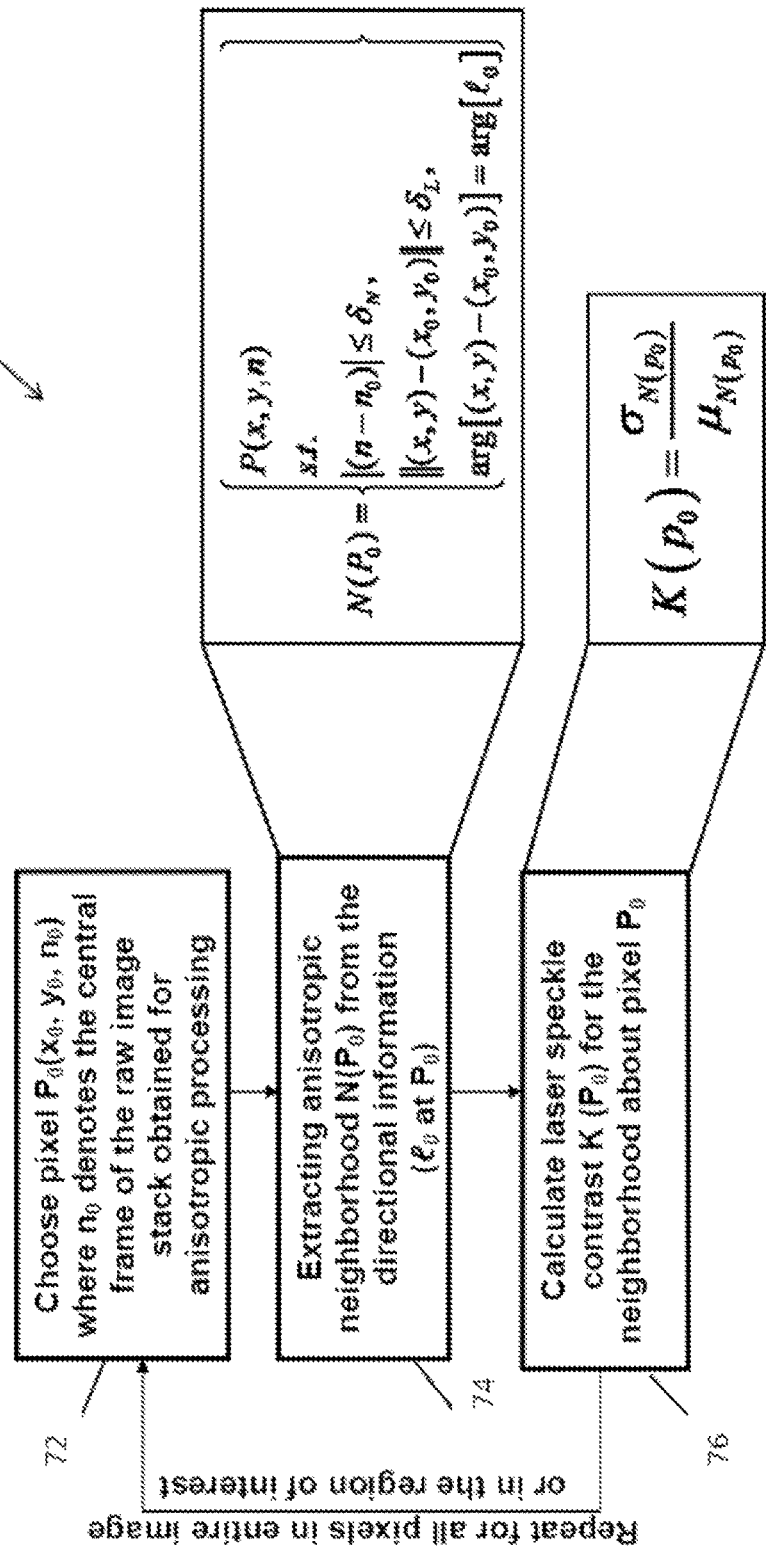
FIG. 4 illustrates a flow diagram of a method of implementation of the anisotropic processing scheme, according to an embodiment of the present invention.

FIG. 4 illustrates a flow diagram of a method of implementation of the anisotropic processing scheme, according to an embodiment of the present invention. The method 70 of FIG. 4, includes a step 72 of choosing a pixel $P_0(x_0, y_0, n_0)$ 20 where $n_0$ denotes a central frame of the raw image stack obtained for anisotropic processing. For every such pixel $P_0(x_0, y_0, n_0)$ in the stack of $n=1:N_F$ sequentially acquired raw laser speckle image frames, step 74 is used to extract the neighborhood $N(P_0)$ relevant to aLSCI, and defined as the set of pixels that lie along the line $l_0$ within $\pm\delta_L$ pixels about the central pixel $P(x_0, y_0, n)$ in each of $N_F$ frames positioned around the central frame $n_0$. Here, $\delta_L=\frac{1}{2}(L_N-1)$ in pixels, with $L_N$ being length of the line neighborhood and $l_0$ is the supervised direction calculated for pixel $P_0$. Similarly, the temporal neighborhood on either side of the central frame is defined by $\delta_N=\frac{1}{2}(N_F-1)$. The line $l_0$ is defined as the direction of blood flow at each pixel $P_0$. This can be done with the algorithm reproduced below.

$$N(P_0) = \left\{ \begin{array}{c} P(x, y, n) \\ \text{such that} \\ |(n - n_0)| \leq \delta_N, \\ \|(x, y) - (x_0, y_0)\| \leq \delta_L, \\ \arg[(x, y) - (x_0, y_0)] = \arg[l_0] \end{array} \right\}$$

Where n denotes the frame number in the acquired image stack, (x, y) denote pixel coordinates in the image plane, $P_0(x_0, y_0, n_0)$ is the pixel of interest chosen, $l_0$ is the direction of the blood flow at $P_0$, while $\delta_N$ and $\delta_L$ are predetermined parameters that govern the number of frames and number of pixels in each frame respectively that are used for processing. Step 76 includes calculating laser speckle contrast $K(P_0)$ for the neighborhood around $P_0$, using the algorithm below.

$$K(p_0) = \frac{\sigma_{N(p_0)}}{\mu_{N(p_0)}}$$

Where $\sigma_{N(P^0)}$ and $\mu_{N(P^0)}$ are the standard deviation and mean respectively of the intensity of all pixels in a defined local neighborhood $N(P_0)$.

These steps can be repeated for all pixels in the entire image or just those pixels in an area of interest. Also, these steps may be carried out for multiple pixels simultaneously through the use of matrix manipulations. Further, these steps can be carried out manually or with a computing device, processor, or any other means of carrying out the steps known to or conceivable by one of skill in the art.

Further with respect to FIG. 4, anisotropic LSCI is based on calculating speckle contrast preferentially along the direction of blood flow, as shown in FIG. 2. It is notable that this preferred implementation of the anisotropic methodology described with respect to FIGS. 2-4 considers only planar or linear neighborhoods. In general, the present invention and methodology could utilize a neighborhood having an orientation that is non-, curvi- or piece wise-linear with respect to pixel connectivity, but aligned along the direction of blood flow. This is depicted in FIG. 5, described, below.

Figure 5:
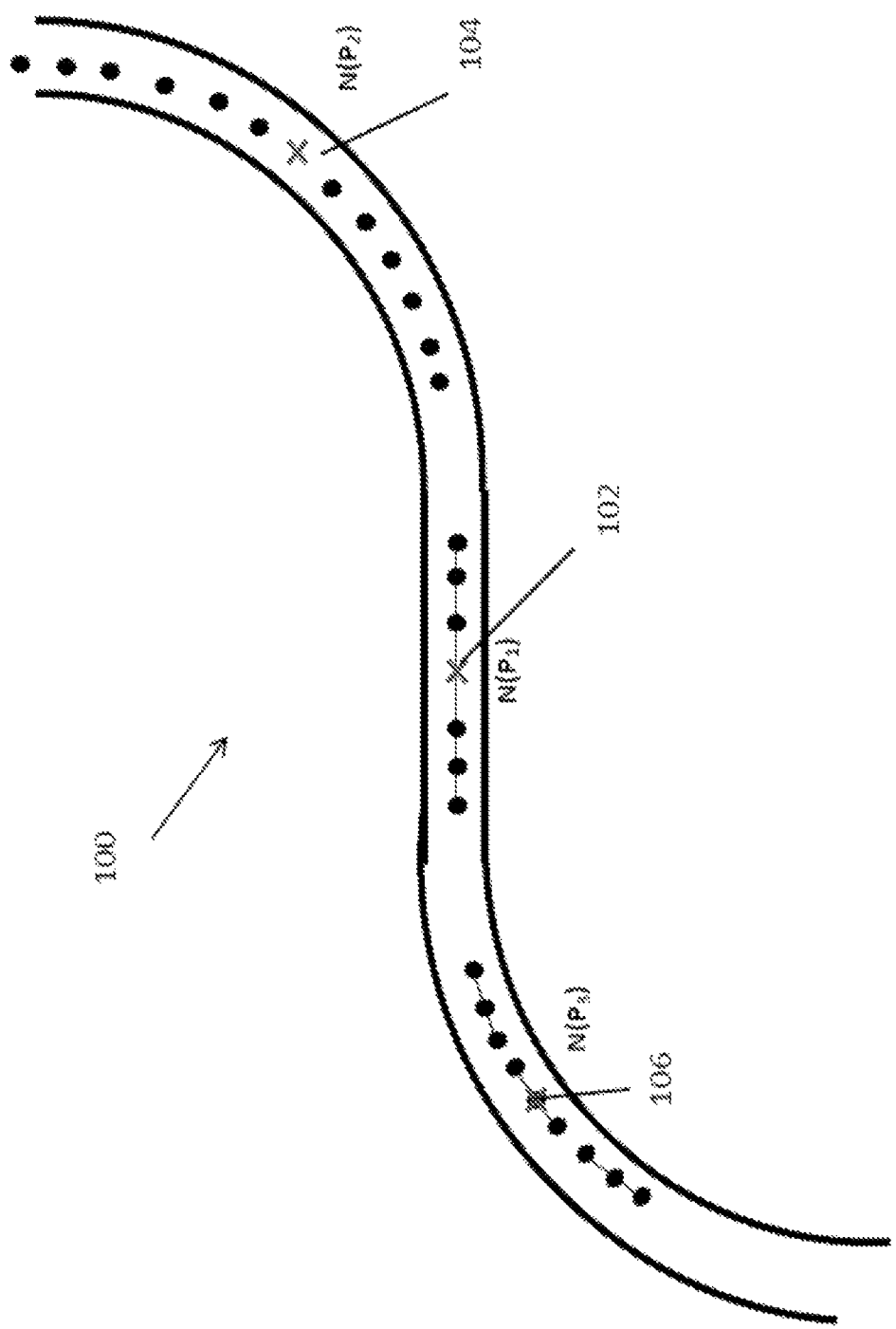
FIG. 5 illustrates a schematic view of different types of anisotropic pixel neighborhoods over which speckle contrast can be calculated according to an embodiment of the present invention.

FIG. 5 illustrates a schematic view of different types of anisotropic pixel neighborhoods over which speckle contrast can be calculated. FIG. 5 illustrates a blood vessel 100 containing examples of different anisotropic pixel neighborhoods, $N(P_1)$ 102, $N(P_2)$ 104, and $N(P_3)$ 106. In a general formulation, the anisotropic neighborhood, N(P) at the pixel of interest P, is a surface in the spatio-temporal domain. The projection of N(P) in the image plane (spatial domain) can include a finite number of pixels best connected through a line segment such as $N(P_1)$ 102 (also described with respect to FIG. 3) or through a polynomial curve segment such as $N(P_2)$ 104, or through a piece-wise linear segment such as $N(P_3)$ 106. A curve segment neighborhood, as exemplified by $N(P_2)$ 104, is expected to reduce the error in estimating the speckle contrast in case of small curvy vessels or also, long but tortuous vessels. Note that FIG. 5 shows only the spatial connectivity between pixels in the central frame of the image stack chosen for aLSCI. In the temporal domain, N(P) comprises pixels with the same spatial coordinates as in the central frame, chosen from remainder of temporally acquired frames designated to be utilized for anisotropic processing.

It is also possible to implement the aLSCI system and method, according to an embodiment of this invention, in a manner that utilizes only one image frame for calculation of anisotropic laser speckle contrast. In such an embodiment, the neighborhood of pixels N(P) utilized for anisotropic processing would be a line or a curve and not a surface. Likewise, it is also not necessary that the neighborhood of pixels chosen for anisotropic speckle contrast processing be single pixel thin that is, be planar or be a surface. The neighborhood can comprise of multiple adjacent parallel planes or surfaces of pixels in the spatio-temporal domain, but the spatial orientation must be anisotropic and preferentially aligned along the direction of flow.

A method of extracting the direction of blood flow at the pixel of interest $P_0$ 20, that is, different methods of implementing Step 62 of FIG. 3 can also be used. These methods of extracting directional information are explained in the context of a planar neighborhood of pixels that is, neighborhood of type $N(P_1)$ 102 of FIG. 5. Note that the can also be generalized to curved segments, as illustrated by $N(P_2)$ 104 and $N(P_3)$ 106 of FIG. 5, as would be known to or conceivable by one of skill in the art. Different methods of obtaining directional information could also be used, as known to or conceivable by one of skill in the art. The line $l_0$ is defined as the direction of blood flow at each pixel $P_0$ and could be obtained using multiple techniques, as known to or conceivable by one of skill in the art. Several preferred methods of achieving the direction of blood flow are listed below:

a) A possible method is to choose a direction (from a multitude of considered directions) along which the variation of pixel intensities is minimum, as the direction of flow at the pixel under consideration. Said pixel intensities may be constituted by intensities of pixels in either one or many image frames in the raw speckle image stack; or may also be constituted by the intensities of pixels in processed images such as the mean image of the entire raw image stack or the reference image 60. For example, the square error of intensity variation in the reference image around the pixel of interest within a line segment of length $l_0$ can be minimized across various directions to obtain the direction of blood flow as:

$$\arg[l_0] = \underset{l \in 0^0 \to 180^0}{\operatorname{argmin}} \left[ \sum_{P \in l} (K_P - K_{P_0})^2 \right]$$

Where $K_P$ and $K_{P0}$ are speckle contrast values of an arbitrary pixel P in the line neighborhood and the pixel of interest $P_0$. Instead of minimizing square error between the values at P and $P_0$, the technique can be generalized to minimize a similar function of the neighborhood intensities, as deemed appropriate for the application.

b) Another possible approach of estimating the direction of blood flow is to calculate the speckle contrast in the stack of raw speckle images along each possible direction. And at each pixel, the direction along which the speckle contrast is minimum can be chosen as the direction of flow for that pixel.

c) In general, the direction of blood flow can be obtained either using a supervised or an unsupervised scheme.

c1) In a supervised scheme of determining blood flow direction, directions can be estimated either manually or using a feature based approach such as edge detection or ridge based detection, curvature analysis and region growing approaches on reference speckle-contrast images obtained using any of the processing schemes or on reflectance or fluorescence images of the region of interest acquired under white light or spectrally filtered illumination.

c2) In an unsupervised scheme of determining blood flow direction, directions are extracted based on the minimum contrast obtainable at the location while traversing all possible directions or a pre-computed set of likely directions. The direction of flow at pixel $P_0(x_0,y_0,n_0)$ can be defined in the imaging plane as $N_{1D}$:

$$N_{1d}(P_0)=\{P(x,y,n) s.t. |P-P_0|\leq\delta_S \text{ and } (P-P_0)\times \widehat{V_0}\times=0\}$$

where $2\delta_s$ is the length of the line segment in spatial domain, while $\hat{v}_0$ is a unit vector in the direction of the blood flow at $P_0(x_0, y_0)$. The equation $$K(p_0) = \frac{\sigma_{N(p_0)}}{\mu_{N(p_0)}}$$

is used to calculate the local $K(P_0)$. The direction of mean flow given by $\hat{v}_0$ at each point is determined by considering the variation of $K(P_0)$ calculated along all possible directions at that point. The minimum K value demonstrates the maximum blur and hence the direction of actual flow. Thus, $\hat{v}_0$ is chosen such that $$\arg(\hat{v}_0)=\theta_{dir}=\arg \min\{K_{1d(P_0,\theta)}\}$$

Where $N_{1d}(P_0, \theta)$ describes a similar neighborhood as $N_{1d}(P_0)$ but at an arbitrary $\theta$ direction.

d) In a non-linear scheme of estimating non-linear directions, though the direction of blood flow at a pixel has a linear fixed orientation, the direction of blood flow along every pixel in the chosen neighborhood may not possess the same orientation. The neighborhood may be chosen along a possible non-linear (curvilinear) axial direction of the blood vessel that is, a set of pixels that may connect through a smooth or piecewise linear curve (not a line) in the plane of the vessel or equivalently a surface (not a plane) in three-dimensional space.

The aLSCI technique uses information regarding direction of blood flow to improve image quality. The aLSCI method described herein, is a departure from conventional isotropic means of processing laser speckle images and provides improvement over them in terms of spatio-temporal resolution, contrast-to-noise ratio and accuracy of flow measurements. The aLSCI technique described herein ensures a theoretical spatial resolution of 1 pixel along the cross-section of vessels, thereby leading to greater distinguishability of micro-vessels.

The aLSCI technique described herein can also achieve a high temporal resolution since it can utilize, but is not be limited to utilizing as few as three image frames for calculating contrast values. This is directly useful for imaging of rapid changes in physiology (blood flow or other direct, indirect or empirical measures of blood flow) or indirectly useful for imaging as fewer number of frames help reduce inter-frame inconsistencies such as motion artifact. Thus, aLSCI is useful for imaging in noisy (as regards to motion and other imaging artifacts) environments like the clinic or even imaging un-restrained animals for research. The possible use of fewer image frames in aLSCI reserves the potential to reduce total image acquisition times and consequently, reduce the total exposure of the target tissue to incident illumination. Thus, the aLSCI invention becomes suitable for imaging light-sensitive tissue such as the retina. The aLSCI technique is expected to provide significant improvement in image quality over other techniques that achieve the same temporal resolution. Image quality could mean that the contrast-to-noise ratio with which microvessels are imaged is better as well as the accuracy by which flow is represented in both vessels regions as well as background tissue perfusion, is improved.

The aLSCI imaging system could allow further handling of the image data. Image data includes any combination of some or all of the raw speckle images, some or all of the anisotropic laser speckle contrast image, some or all of any intermediate image or other intermediate information such as anisotropic local neighborhoods or directional information about blood flow. Another embodiment of the invention can include devices for tasks such as display or printing of image data. The display device could be, but is not limited to be, a computer monitor or a handheld phone screen. Another embodiment of the invention can include devices for storage of image data temporarily or long term. Examples of data storage devices are flash memory and hard disk drives, though any data storage device that suits the requirements of the application, as determined by one of skill in the art, can be used. Yet another embodiment of the invention can include devices and methods for transmission of image data to remote locations for further use or storage. The transmission of data could be over wired or wireless communication channels or both to suit the application, as determined by one of skill in the art. Still another embodiment of the invention can include an interface device that will allow the user to input or change imaging parameters to suit the requirements of the application.

EXAMPLE

The following discussion is included merely by way of example. It is provided to illustrate the methods and system set forth and discussed above. This example, therefore, is not meant to be considered limiting to the scope and application of the methods and systems described above. Further, any application know to or conceivable by one of skill in the art could also be used with the above described methods and systems.

Figure 6:
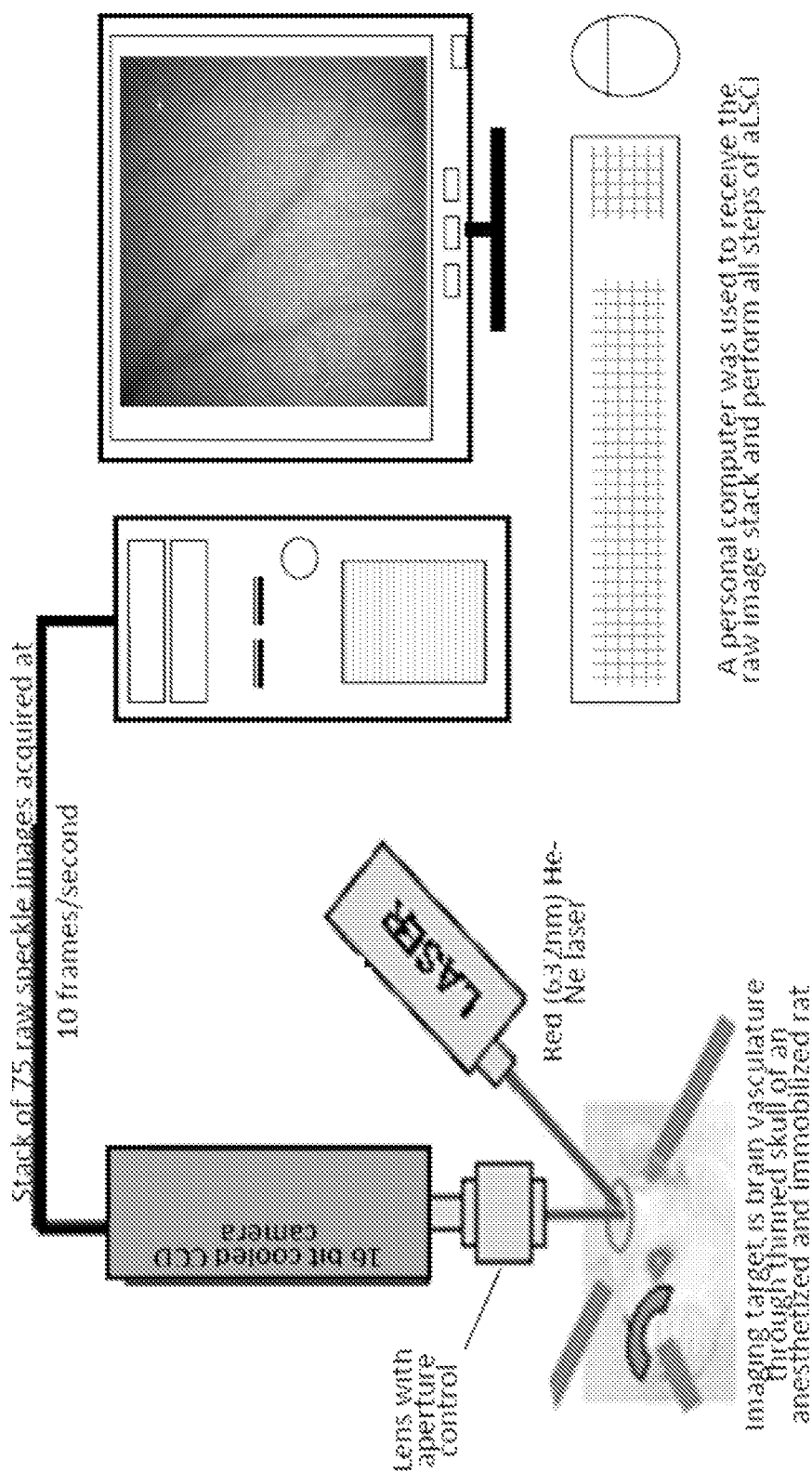
FIG. 6 illustrates a diagram of an aLSCI apparatus and protocol for acquiring images of rat brain vasculature through a thinned skull preparation in an anesthetized rat.

As an exemplary embodiment, the anisotropic laser speckle contrast imaging (aLSCI) invention was implemented and characterized in a rat brain model of microvascular imaging. This embodiment involved the use of 632 nm (red) He Ne laser illumination and a 16 bit cooled CCD camera for image acquisition, as shown in FIG. 6. The optical assembly provided a magnification of 1:1 and numerical aperture (f-number) of 4.0 thus producing speckles ~12.45 micrometers in diameter, which is approximately twice our pixel size of 6.7 micrometers. A stack of 75 raw speckle images was acquired at 10 frames/sec. The imaging target was the brain vasculature of an anesthetized rat through a thinned skull.

Directional information at every pixel was inferred by estimating the direction of minimal contrast gradient at $P_0$ in a baseline tLSCI image obtained by processing 75 raw speckle frames. For improving the accuracy of resulting supervised directions, the tLSCI image was histogram equalized prior to further calculations. As a finite line segment of length $L_N$ pixels ($L_N \geq 3$) was considered, direction of minimal intensity gradient is evaluated as the line along which minimal intensity variation with respect to the central pixel is observed. This is calculated using least square error about the central pixel value as the line segment rotates 180° about the central pixel, as indicated by:

$$\arg[\ell_0] = \underset{\ell \in 0^0 \to 180^0}{\mathrm{argmin}} \left[ \sum_{P \in \ell} (K_P - K_{P_0})^2 \right]$$

Where $K_P$ and $K_{P0}$ are speckle contrast values of an arbitrary pixel P in the line neighborhood and the pixel of interest $P_0$.

In this exemplary embodiment and experiment, the pixel neighborhood $N(P_0)$ comprised a total of 27 pixels that were chosen from 3 time-adjacent image frames such that 9 pixels with same spatial coordinates were chosen from each frame and included the pixel of interest $P_0$ and 4 pixels on either side of $P_0$ along the estimated direction of blood flow $l_0$. Anisotropic laser speckle contrast was calculated in this set of local neighborhood pixels by dividing the standard deviation of all pixels in $N(P_0)$ by the mean of all pixels in $N(P_0)$.

Figure 7:
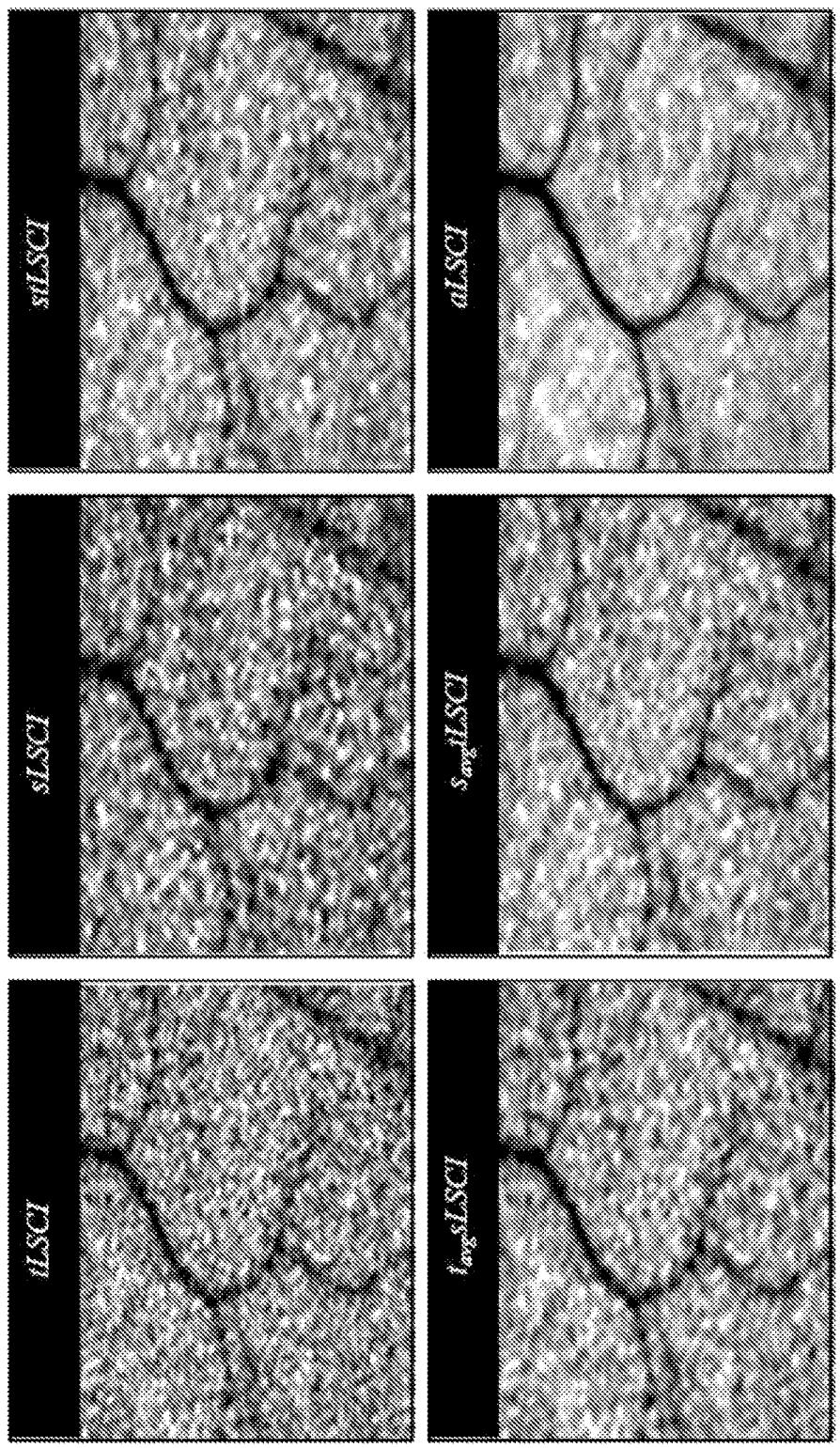
FIG. 7 illustrates an example aLSCI image with higher vessel-to-background contrast and microvessel distinguishability than other concurrent speckle contrast processing schemes.

In this exemplary embodiment and experiment, said directional information, neighborhood and speckle contrast was obtained similarly for every pixel in the image; and an aLSCI image was made by plotting the anisotropic laser speckle contrast values at every pixel in grayscale. FIG. 7 shows an example aLSCI image, obtained through implementing the said embodiment of the current invention, and compares it to speckle contrast images obtained using traditional processing schemes.

For the exemplary embodiment, it was shown that aLSCI achieves a higher level of microvessel distinguishability in high temporal resolution laser speckle imaging as compared to traditional spatiotemporal schemes. aLSCI achieved a 15% improvement in contrast to noise ratio (an indicator of the capacity to distinguish microvessels from background tissue regions) over the best of conventional LSCI schemes. Further, aLSCI can visualize background tissue perfusion patterns with less noise than other LSCI methods. The present embodiment of aLSCI achieved a 23% suppression in background noise levels compared to the best among other LSCI methods. Additionally, aLSCI has a higher accuracy in representing blood flow over other speckle contrasting schemes. In the current embodiment of aLSCI, it achieved a 6% higher level of accuracy over other LSCI schemes. With these strong features, aLSCI can be utilized to image rapidly fluctuating blood flow patterns with improved fidelity over other schemes of speckle contrasting. In the assessed embodiment, aLSCI was used to analyze blood flow fluctuations due to forepaw electrical stimulation in a rat model as well as the heart rate associated pulsation. aLSCI proved to monitor these quantities with 48% and 23% higher signal to noise ratios when compared to other LSCI schemes.

Because the aLSCI invention can be programmed to require as few as three frames for contrast calculation, the technique can lend itself to applications where acquisition time is of prime importance. For example, in case of retinal imaging, a smaller total acquisition time may help limit the amount of laser exposure at the retina or conversely, allow for usage of a higher intensity beam for a shorter time. The aLSCI invention also helps address the problem of motion artifact not only through quicker acquisition times, but also by significantly reducing the computational complexity and burden of compensatory inter-frame registration schemes.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

More specifically, it should be noted that, the aLSCI technique could be applied to imaging of various tissues either clinically or in the laboratory for a variety of reasons. The aLSCI technique can be used to improve laser speckle contrast imaging method with an emphasis on applications that involve, at least, but are not limited to: imaging of rapid changes in vascular morphology or blood flow, such as heart rate dependent pulsatility of blood flow; imaging of the retina where acquisition of fewer image frames would reduce the total laser energy incident on the retina; imaging in natural environments where the target tissue may not be stationary and thus, reducing the number of frames would allow the handling of noise artifact more effectively; imaging of background tissue perfusion, or capillary blood flow in tissue, which can be imaged at a high temporal resolution with higher contrast and accuracy. The use of the aLSCI system and method is not to be restricted to any particular type of tissue and is applicable to imaging of the brain, skin, bone, retina, muscle, heart and lungs amongst other tissues. Similarly, the use of the aLSCI system and method may not be restricted to use in humans, and may also be applicable to any vascularized living organism. aLSCI may find application not only in monitoring normal tissue, but also abnormal tissue, including various cases of disease and pathophysiology occurring naturally or even tissue altered through therapy, experimentation or preparation for imaging.

It should also be noted that the methods herein describe contrast calculation using as few as three frames. However, this "number of frames" should not be restrictive for the use of the methodology. In general, the concept can also be extrapolated to even a single frame whereby blood flow directions are calculated using any method described above and contrast is calculated using pixels along the calculated directions only within that frame. Similarly, the same concept could be used while increasing the number of utilized frames to as many as five hundred or even a few thousand images. The image quality depends on the number of frames used and the preferred embodiment will use three frames.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A system for creating a laser speckle contrast image, comprising:
   a device configured for the acquisition of at least one raw laser speckle image;
   a processor configured to receive the at least one raw laser speckle image and further programmed to:
   a) select a primary pixel in one of the at least one raw laser speckle image;
   b) determine a direction of a blood flow at said primary pixel;
   c) identify an anisotropic neighborhood that is aligned along the direction of blood flow at said primary pixel; said anisotropic neighborhood comprising a collection of pixels, wherein one pixel of said collection of pixels is said primary pixel;
   d) calculate a speckle contrast value at said primary pixel within the anisotropic neighborhood;

said processor being programmed to do steps a-d at least once, wherein additional iterations beyond a first iteration involve a different primary pixel; and e) generate a laser speckle contrast image using the speckle contrast value(s).

2. The system of claim 1 wherein the device configured for the acquisition of the at least one raw laser speckle image further comprises a source of coherent illumination, an optical assembly, and an image acquisition system.

3. The system of claim 2 wherein at least one of:
(a) the source of coherent illumination further comprises one selected from a group consisting of a gas laser, a diode laser, and a pulsed laser or
(b) the device configured for the acquisition of the at least one raw laser speckle image comprises a light source having one or more wavelengths of illumination in a range of approximately 200 nm to approximately 2000 nm.

4. The system of claim 2 wherein the image acquisition system comprises one selected from a group consisting of a charge coupled device (CCD) cameras, metal oxide semiconductor (MOS), complementary MOS (CMOS) cameras, photodiodes, phototransistors, and photo tubes.

5. The system of claim 1, wherein a plurality of raw laser speckle images are acquired and each of said plurality of raw laser speckle images are processed to yield the laser speckle contrast image.

6. The system of claim 1 wherein the processor comprises one selected from a group consisting of computers, microprocessors, microcontrollers, field programmable gate arrays (FPGA), complex programmable logic devices (CPLD), and application specific integrated circuits (ASIC).

7. The system of claim 1, wherein the collection of pixels are aligned along the direction of blood flow.

8. The system of claim 7, wherein the processor is further configured to calculate the speckle contrast value as a ratio of standard deviation of all pixel intensities within the collection of pixels over the mean of all pixels intensities within the collection of pixels within the anisotropic neighborhood.

9. The system of claim 1 further comprising at least one of:
(a) the anisotropic neighborhood being planar in a spatio-temporal domain and mathematically expressible in a form:

$$N(P_0) = \begin{Bmatrix} P(x, y, n) \\ \text{such} \ldots \text{that} \\ |(n - n_0)| \leq \delta_N, \\ \|(x, y) - (x_0, y_0)\| \leq \delta_L, \\ \arg[(x, y) - (x_0, y_0)] = \arg[\ell_0] \end{Bmatrix}$$

where n denotes a frame number in an acquired image stack, (x, y) denote pixel coordinates in an image plane, $N(P_0)$ is the anisotropic neighborhood comprising a set of secondary pixels P with coordinates (x, y, n) around primary pixel $P_0$ with coordinates $(x_0, y_0, n_0)$, and $\ell_0$ represents a direction of the blood flow at $P_0$, while $\delta_N$ and $\delta_L$ are predetermined parameters that govern a number of frames and a number of pixels in each frame respectively that are used for processing;
(b) the anisotropic neighborhood taking a form of one or more of adjacent surfaces of pixels in a spatio-temporal domain that are aligned along the direction of blood flow and in a manner that a projection of each surface in a plane of the raw laser speckle image is a smooth curve; or
(c) the anisotropic neighborhood taking a form of one or more composite collections of piece-wise planar neighborhoods of pixels in a spatio-temporal domain that are aligned along the direction of blood flow and in a manner that a projection of each surface in a plane of the raw laser speckle image is piece-wise linear.

10. The system of claim 1 wherein the system is used for an application selected from a group consisting of imaging of blood flow in tissue, imaging of vascular morphology in tissue, imaging of changes in vascular morphology in tissue, imaging of changes in blood flow in tissue, imaging of the tissue in natural form, imaging the tissue in an altered form, imaging of tissue that is stabilized using anesthesia, imaging of tissue that is stabilized using paralytics, imaging tissue that is not stabilized, and imaging of tissue perfusion in a manner that blood vessels are not discernible to the human eye but blood flow is discernible.

11. The system of claim 1, wherein the system can be used to yield a plurality of laser speckle contrast images.

12. A method for creating a laser speckle contrast image, comprising:
a) acquiring at least one raw laser speckle image;
b) selecting a primary pixel in one of the at least one raw laser speckle image;
c) determining a direction of blood flow at the primary pixel;
d) identifying an anisotropic neighborhood that is aligned along the direction of blood flow at said primary pixel; said anisotropic neighborhood comprising a collection of pixels, wherein one of said collection of pixels is said primary pixel
e) calculating a speckle contrast value at the primary pixel within the anisotropic neighborhood;

steps b-e being performed at least once, wherein additional iterations beyond a first iteration involve a different primary pixel; and f) generating a laser speckle contrast image using the speckle contrast value(s).

13. The method of claim 12 wherein the at least one raw laser speckle image may be acquired under illumination comprising one or more wavelengths lying in the approximate range of 200 nm to 2000 nm.

14. The method of claim 12 wherein a plurality of raw laser speckle images are acquired and said plurality of raw laser speckle images are processed to yield the laser speckle contrast image.

15. The method of claim 12 further comprising estimating the direction of blood flow using information about an axial direction of blood vessels calculated for each pixel that lies inside a vessel.

16. The method of claim 12, comprising calculating the speckle contrast value as a ratio of standard deviation of all pixel intensities within the collection of pixels over the mean of all pixels intensities within the collection of pixels within the anisotropic neighborhood.

17. The method of claim 12 further comprising at least one of:
(a) extracting the anisotropic neighborhood which is planar in a spatio-temporal domain and mathematically expressible in a form:

$$N(P_0) = \left\{ \begin{array}{c} P(x, y, n) \\ \text{such} \ldots \text{that} \\ |(n - n_0)| \leq \delta_N, \\ \|(x, y) - (x_0, y_0)\| \leq \delta_L, \\ \arg[(x, y) - (x_0, y_0)] = \arg[l_0] \end{array} \right\}$$

where n denotes a frame number in an acquired image stack, (x, y) denote pixel coordinates in an image plane, $N(P_0)$ is the anisotropic neighborhood comprising a set of secondary pixels P with coordinates (x, y, n) around primary pixel $P_0$ with coordinates $(x_0, y_0, n_0)$, and $l_0$ represents a direction of the blood flow at $P_0$, while $\delta_N$ and $\delta_L$ are predetermined parameters that govern a number of frames and a number of pixels in each frame respectively that are used for processing;

(b) extracting an anisotropic neighborhood that takes a form of one or more of multiple adjacent surfaces of pixels in a spatio-temporal domain that are aligned along the direction of blood flow and in a manner that a projection of the surface in the plane of the raw laser speckle image may be a smooth curve;

(c) extracting an anisotropic neighborhood that is one or more composite collections of piece-wise planar neighborhoods of pixels in a spatio-temporal domain that are aligned along the direction of blood flow and in a manner that the projection of a surface in a plane of the raw laser speckle image is piece-wise linear.

18. The method of claim 12, wherein said determination of direction of blood flow comprises the use of a method selected from a group consisting of manual estimation, ridge based detection, curvature analysis, and region growing approach.

19. The method of claim 12, wherein said determination of direction of blood flow comprises selecting the direction of blood flow with minimum spatial contrast of pixel intensities incurred in the neighborhood of the said primary pixel while traversing directions of blood flow.

\* \* \* \* \*